United States Patent
Silberman et al.

(10) Patent No.: US 11,559,279 B2
(45) Date of Patent: Jan. 24, 2023

(54) METHODS AND APPARATUSES FOR GUIDING COLLECTION OF ULTRASOUND DATA USING MOTION AND/OR ORIENTATION DATA

(71) Applicant: BFLY Operations, Inc., Guilford, CT (US)

(72) Inventors: Nathan Silberman, Brooklyn, NY (US); Tomer Gafner, Great Neck, NY (US); Igor Lovchinsky, New York, NY (US); Ardavan Saeedi, Jersey City, NJ (US)

(73) Assignee: BFLY OPERATIONS, INC., Burlington, MA (US)

( * ) Notice: Subject to any disclaimer, the term of this patent is extended or adjusted under 35 U.S.C. 154(b) by 403 days.

(21) Appl. No.: 16/529,867

(22) Filed: Aug. 2, 2019

(65) Prior Publication Data

US 2020/0037987 A1 Feb. 6, 2020

Related U.S. Application Data

(60) Provisional application No. 62/714,622, filed on Aug. 3, 2018.

(51) Int. Cl.
*A61B 8/00* (2006.01)
*A61B 5/00* (2006.01)

(52) U.S. Cl.
CPC .......... *A61B 8/4254* (2013.01); *A61B 5/7267* (2013.01); *A61B 8/46* (2013.01)

(58) Field of Classification Search
CPC ................................ A61B 8/4254; A61B 8/58
See application file for complete search history.

(56) References Cited

U.S. PATENT DOCUMENTS

| 7,867,167 B2 | 1/2011 | Boctor et al. |
| 8,756,033 B2 | 6/2014 | Ishikawa et al. |
| 8,852,103 B2 | 10/2014 | Rothberg et al. |

(Continued)

FOREIGN PATENT DOCUMENTS

| WO | WO 2017/222970 A1 | 12/2017 |
| WO | WO 2018/094118 A1 | 5/2018 |

OTHER PUBLICATIONS

International Search Report and Written Opinion dated Oct. 25, 2019 in connection with International Application No. PCT/US2019/044777.

(Continued)

*Primary Examiner* — Bill Thomson
*Assistant Examiner* — Aminah Asghar
(74) *Attorney, Agent, or Firm* — Osha Bergman Watanabe & Burton LLP

(57) ABSTRACT

Aspects of the technology described herein relate to guiding collection of ultrasound data collection using motion and/or orientation data. A first instruction for rotating or tilting the ultrasound imaging device to a default orientation may be provided. Based on determining that the ultrasound imaging device is in the default orientation, a second instruction for translating the ultrasound imaging device to a target position may be provided. Based on determining that the ultrasound imaging device is in the target position, a third instruction for rotating or tilting the ultrasound imaging device to a target orientation may be provided.

20 Claims, 8 Drawing Sheets

(56) References Cited

U.S. PATENT DOCUMENTS

| | | |
|---|---|---|
| 9,521,991 B2 | 12/2016 | Rothberg et al. |
| 9,592,030 B2 | 3/2017 | Rothberg et al. |
| 10,628,932 B2 | 4/2020 | Rothberg et al. |
| 10,702,242 B2 | 7/2020 | de Jonge et al. |
| 10,706,520 B2 | 7/2020 | Rothberg et al. |
| 10,893,850 B2 | 1/2021 | Gafner et al. |
| 2006/0176242 A1 | 8/2006 | Jaramaz et al. |
| 2011/0055447 A1 | 3/2011 | Costa |
| 2016/0174934 A1* | 6/2016 | Cong ............... A61B 8/08 600/459 |
| 2016/0331353 A1 | 11/2016 | Ralston et al. |
| 2017/0105701 A1 | 4/2017 | Pelissier et al. |
| 2017/0238907 A1* | 8/2017 | Kommu Chs ......... A61B 8/469 |
| 2017/0360397 A1 | 12/2017 | Rothberg et al. |
| 2017/0360401 A1 | 12/2017 | Rothberg et al. |
| 2017/0360402 A1 | 12/2017 | de Jonge et al. |
| 2017/0360403 A1 | 12/2017 | Rothberg et al. |
| 2017/0360404 A1 | 12/2017 | Gafner et al. |
| 2017/0360411 A1 | 12/2017 | Rothberg et al. |
| 2017/0360412 A1 | 12/2017 | Rothberg et al. |
| 2018/0132724 A1 | 5/2018 | Waechter-Stehle et al. |
| 2019/0038260 A1 | 2/2019 | Lee et al. |
| 2019/0056693 A1 | 2/2019 | Gelman et al. |
| 2019/0130554 A1 | 5/2019 | Rothberg et al. |
| 2019/0142388 A1 | 5/2019 | Gonyeau et al. |
| 2019/0196600 A1 | 6/2019 | Rothberg et al. |
| 2019/0239850 A1 | 8/2019 | Dalvin et al. |
| 2019/0261957 A1 | 8/2019 | Zaslavsky et al. |
| 2019/0266716 A1 | 8/2019 | Rothberg et al. |
| 2019/0282208 A1 | 9/2019 | Silberman et al. |
| 2019/0307428 A1 | 10/2019 | Silberman et al. |
| 2020/0037986 A1 | 2/2020 | Silberman et al. |
| 2020/0037987 A1 | 2/2020 | Silberman et al. |
| 2020/0037998 A1 | 2/2020 | Gafner et al. |
| 2020/0046322 A1 | 2/2020 | Silberman et al. |
| 2020/0054307 A1 | 2/2020 | Silberman et al. |
| 2020/0060658 A1 | 2/2020 | Gafner et al. |
| 2020/0211174 A1 | 7/2020 | Rothberg et al. |
| 2020/0214672 A1 | 7/2020 | de Jonge et al. |
| 2020/0214674 A1 | 7/2020 | Gafner et al. |
| 2020/0214679 A1 | 7/2020 | Silberman et al. |
| 2020/0261054 A1 | 8/2020 | Silberman et al. |
| 2020/0289094 A1 | 9/2020 | de Jonge et al. |
| 2020/0320694 A1 | 10/2020 | Howell et al. |

OTHER PUBLICATIONS

International Preliminary Report on Patentability dated Feb. 18, 2021 in connection with International Application No. PCT/US2019/044786.

International Preliminary Report on Patentability dated Feb. 18, 2021 in connection with International Application No. PCT/US2019/044777.

International Preliminary Report on Patentability dated Feb. 18, 2021 in connection with International Application No. PCT/US2019/044774.

International Search Report and Written Opinion dated Oct. 7, 2019 in connection with International Application No. PCT/US2019/044774.

International Search Report and Written Opinion dated Oct. 29, 2019 in connection with International Application No. PCT/US2019/044786.

* cited by examiner

METHODS AND APPARATUSES FOR GUIDING COLLECTION OF ULTRASOUND DATA USING MOTION AND/OR ORIENTATION DATA

CROSS-REFERENCE TO RELATED APPLICATIONS

The present application claims the benefit under 35 USC § 119(e) of U.S. Patent Application Ser. No. 62/714,622, filed Aug. 3, 2018, and entitled "METHODS AND APPARATUSES FOR GUIDING COLLECTION OF ULTRASOUND DATA USING MOTION AND/OR ORIENTATION," which is hereby incorporated herein by reference in its entirety.

FIELD

Generally, the aspects of the technology described herein relate to ultrasound data collection. Some aspects relate to guiding collection of ultrasound data using motion and/or orientation data from an ultrasound imaging device.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using an ultrasound imaging device), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect, a method includes providing, by a processing device in operative communication with an ultrasound imaging device, a first instruction for rotating or tilting the ultrasound imaging device to a default orientation; based on determining that the ultrasound imaging device is in the default orientation, providing a second instruction for translating the ultrasound imaging device to a target position; and based on determining that the ultrasound imaging device is in the target position, providing a third instruction for rotating or tilting the ultrasound imaging device to a target orientation.

In some embodiments, providing the first instruction for rotating or tilting the ultrasound imaging device to the default orientation includes receiving first motion and/or orientation data from the ultrasound imaging device, wherein the first motion and/or orientation data provides an indication of a first motion and/or orientation of the ultrasound imaging device; determining, based on the first motion and/or orientation data, that the ultrasound imaging device is not in the default orientation; and providing the first instruction for rotating or tilting the ultrasound imaging device to the default orientation based on the first motion and/or orientation data. In some embodiments, the ultrasound imaging device is configured to generate the first motion and/or orientation data using one or more of an accelerometer, a gyroscope, or a magnetometer on the ultrasound imaging device. In some embodiments, the default orientation includes a longitudinal axis of the ultrasound imaging device being parallel to gravity; and a longitudinal axis of a sensor of the ultrasound imaging device being perpendicular to a longitudinal axis of a subject being imaged (where the subject being imaged is positioned in some default orientation relative to gravity, such as lying on his/her right side, on his/her left side, or on his/her back). In some embodiments, the method further includes receiving second motion and/or orientation data from the ultrasound imaging device; and determining, based on the second motion and/or orientation data, that the ultrasound imaging device is in the default orientation. In some embodiments, providing the second instruction for translating the ultrasound imaging device to the target position includes receiving first ultrasound data from the ultrasound imaging device; determining, based on the first ultrasound data, that the ultrasound imaging device is not at the target position; and providing the second instruction for translating the ultrasound imaging device to the target position based on the first ultrasound data.

In some embodiments, providing the second instruction for translating the ultrasound imaging device to the target position based on the first ultrasound data includes inputting the first ultrasound data to a statistical model configured to output instructions for moving the ultrasound imaging device based on inputted ultrasound data. In some embodiments, the method further includes receiving, from the statistical model, an instruction corresponding to translating the ultrasound imaging device and an instruction corresponding to rotating or tilting the ultrasound imaging device; and providing, as the second instruction, the instruction corresponding to translating the ultrasound imaging device and not the instruction corresponding to rotating or tilting the ultrasound imaging device. In some embodiments, the statistical model has been trained on training ultrasound data substantially all of which was collected by one or more other ultrasound imaging devices in the default orientation and/or the target position. In some embodiments, the method further includes receiving, subsequent to providing the second instruction, third motion and/or orientation data from the ultrasound imaging device; determining, based on the third motion and/or orientation data, that the ultrasound imaging device is not in the default orientation; and providing a fourth instruction for moving the ultrasound imaging device to the default orientation based on the third motion and/or orientation data. In some embodiments, the method further includes receiving second ultrasound data from the ultrasound imaging device; and determining, based on the second ultrasound data, that the ultrasound imaging device is at the target position.

In some embodiments, providing the third instruction for rotating or tilting the ultrasound imaging device to the target orientation includes determining, based on the second ultrasound data, that the ultrasound imaging device is not in the target orientation; and providing the third instruction for rotating or tilting the ultrasound imaging device to the target orientation based on the second ultrasound data. In some embodiments, providing the third instruction for rotating or tilting the ultrasound imaging device to the target orientation based on the second ultrasound data includes inputting the second ultrasound data to a statistical model configured to output instructions for moving the ultrasound imaging device based on inputted ultrasound data. In some embodiments, the method further includes receiving, from the statistical model, an instruction corresponding to translating the ultrasound imaging device and an instruction corresponding to rotating or tilting the ultrasound imaging device; and providing, as the third instruction, the instruction corresponding to rotating or tilting the ultrasound imaging device and not the instruction corresponding to translating the ultrasound imaging device. In some embodiments, the statistical model has been trained on training ultrasound data substantially all of which was collected by one or more other ultrasound imaging devices in the default orientation and/or the target position. In some embodiments, the method further includes receiving, subsequent to providing the third instruction, third ultrasound data from the ultrasound imaging device; determining, based on the third ultrasound data, that the ultrasound imaging device is not in the target position; and providing a fifth instruction for moving the ultrasound imaging device to the target position based on the third ultrasound data. In some embodiments, the method further includes receiving fourth ultrasound data from the ultrasound imaging device; and determining, based on the fourth ultrasound data, that the ultrasound imaging device is in the target orientation.

According to another aspect, a method includes providing, by a processing device in operative communication with an ultrasound imaging device, instructions for moving the ultrasound imaging device to a target position before providing any instructions for moving the ultrasound imaging device to a target orientation. In some embodiments, providing the instructions for moving the ultrasound imaging device to the target position before providing any instructions for moving the ultrasound imaging device to the target orientation comprises accessing a statistical model configured to output instructions for translation, instructions for rotation, and instructions for tilting of the ultrasound imaging device and suppressing the instructions for rotation and the instructions for tilting of the ultrasound imaging device and providing the instructions for translation of the ultrasound imaging device prior to determining that the ultrasound imaging device is at the target position.

Some aspects include at least one non-transitory computer-readable storage medium storing processor-executable instructions that, when executed by at least one processor, cause the at least one processor to perform the above aspects and embodiments. Some aspects include an apparatus having a processing device configured to perform the above aspects and embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
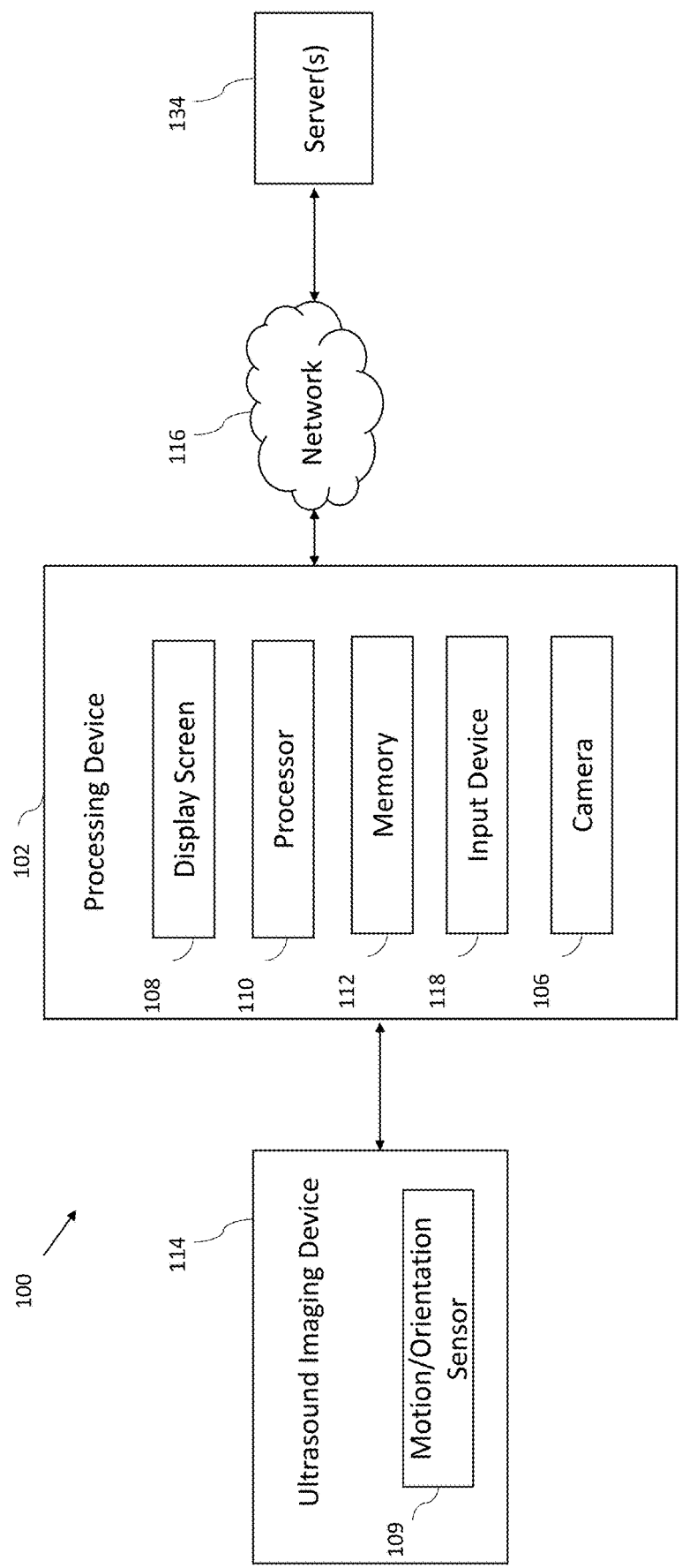
FIG. 1 illustrates a schematic block diagram of an example ultrasound system upon which various aspects of the technology described herein may be practiced.

Ultrasound examinations often include the acquisition of ultrasound images that contain a view of a particular anatomical structure (e.g., an organ) of a subject. Acquisition of these ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may make the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include capturing ultrasound images of the incorrect anatomical structure and capturing foreshortened (or truncated) ultrasound images of the correct anatomical structure.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of ultrasound imaging devices makes them more accessible to the general populace, people who could make use of such devices have little to no training for how to use them. For example, a small clinic without a trained ultrasound technician on staff may purchase an ultrasound device to help diagnose patients. In this example, a nurse at the small clinic may be familiar with ultrasound technology and human physiology, but may know neither which anatomical views of a patient need to be imaged in order to identify medically-relevant information about the patient nor how to obtain such anatomical views using the ultrasound device. In another example, an ultrasound device may be issued to a patient by a physician for at-home use to monitor the patient's heart. In all likelihood, the patient understands neither human physiology nor how to image his or her own heart with the ultrasound device.

Accordingly, the inventors have developed assistive ultrasound imaging technology for guiding an operator of an ultrasound device how to move the ultrasound device relative to an anatomical area of a subject in order to capture medically relevant ultrasound data. The inventors have recognized that it may be helpful to provide instructions for tilting and/or rotating the ultrasound imaging device to a default orientation, and then for a statistical model to provide instructions for translating the ultrasound imaging device to the target position while the ultrasound imaging device is maintained at the default orientation, and then for the statistical model to provide instructions for tilting and/or rotating the ultrasound imaging device to the target orientation while the ultrasound imaging device is maintained at the target position. In other words, the statistical model may only need to provide instructions for translating the ultrasound imaging device to the target position when the ultrasound imaging device is at the default orientation, and may only need to provide instructions for tilting and/or rotating the ultrasound imaging device to the target orientation when the ultrasound imaging device is at the target position. Therefore, in contrast to training a statistical model using training ultrasound data collected by ultrasound imaging devices at a variety of combinations of orientations and positions, it may only be necessary to train the statistical model to provide instructions for translating the ultrasound imaging device to the target position and orientation using training ultrasound data collected by ultrasound imaging devices at (1) a variety of positions but at the single default orientation and (2) a variety of orientations but at the single target position. In other words, the dimensionality of the ultrasound data analyzed by the statistical model may be reduced. The ultrasound training data collected by the ultrasound imaging devices at a variety of positions but at the single, default orientation may be helpful for training the statistical model to provide instructions for translating the ultrasound imaging device to the target position when the ultrasound imaging device is at the default orientation. The training data collected by the ultrasound imaging devices at a variety of orientations but at the single target position may be helpful for training the deep learning mode to provide instructions for tilting and/or rotating the ultrasound imaging device to the target orientation when the ultrasound imaging device is at the target position.

Various aspects of the present application are described as providing or implementing statistical models. In some embodiments, a statistical model may be a convolutional neural network having one or more convolutional layers, a recurrent neural network, a fully-connected neural network, and/or any other suitable type of deep neural network model, a random forest, a support vector machine, a linear classifier, a Bayesian classifier, a non-parametric statistical model, and/or any other statistical model unless otherwise noted.

As referred to herein, a device displaying an item (e.g., a directional indicator on an augmented reality display) should be understood to mean that the device displays the item on the device's own display screen, or generates the item to be displayed on another device's display screen. To perform the latter, the device may transmit instructions to the other device for displaying the item.

As referred to herein, an augmented reality display should be understood to mean any display superimposing non-real two- or three-dimensional graphics on images/video of the real three-dimensional world such that the two- or three-dimensional graphics appear to be present in the three-dimensional world.

As referred to herein, any action performed based on some input criterion/criteria should be understood to mean that the action is performed based solely on the input criterion/criteria or based on the input criterion/criteria and other input criterion/criteria. For example, a determination made based on ultrasound data should be understood to mean that the determination is either made based on the ultrasound data or based on the ultrasound data and other input data.

As referred to herein, a first device that is in operative communication with a second device should be understood to mean that the first device may transmit signals to the second device and thereby affect operation of the second device. The second device may also transmit signals to the first device and thereby affect operation of the first device.

FIG. 1 illustrates a schematic block diagram of an example ultrasound system 100 upon which various aspects of the technology described herein may be practiced. The ultrasound system 100 includes an ultrasound imaging device 114, a processing device 102, a network 116, and one or more servers 134.

The ultrasound imaging device 114 includes a motion and/or orientation sensor 109. The processing device 102 includes a camera 106, a display screen 108, a processor 110, a memory 112, an input device 118, and a motion and/or orientation sensor 109. The processing device 102 is in wired (e.g., through a lightning connector or a mini-USB connector) and/or wireless communication (e.g., using BLUETOOTH, ZIGBEE, and/or WiFi wireless protocols) with the ultrasound imaging device 114. The processing device 102 is in wireless communication with the one or more servers 134 over the network 116.

The ultrasound imaging device 114 may be configured to generate ultrasound data that may be employed to generate an ultrasound image. The ultrasound imaging device 114 may be constructed in any of a variety of ways. In some embodiments, the ultrasound imaging device 114 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound imaging device 114 may include one or more ultrasonic transducers monolithically integrated onto a single semiconductor die. The ultrasonic transducers may include, for example, one or more capacitive micromachined ultrasonic transducers (CMUTs), one or more piezoelectric micromachined ultrasonic transducers (PMUTs), and/or one or more other suitable ultrasonic transducer cells. In some embodiments, the ultrasonic transducers may be formed from or on the same chip as other electronic components (e.g., transmit circuitry, receive circuitry, control circuitry, power management circuitry, and processing circuitry) to form a monolithic ultrasound device. The ultrasound imaging device 114 may transmit ultrasound data and/or ultrasound images to the processing device 102 over a wired (e.g., through a lightning connector or a mini-USB connector) and/or wireless (e.g., using BLUETOOTH, ZIGBEE, and/or WiFi wireless protocols) communication link.

The motion and/or orientation sensor 109 may be configured to generate motion and/or orientation data regarding the ultrasound imaging device 114. For example, the motion and/or orientation sensor 109 may be configured to generate data regarding acceleration of the ultrasound imaging device 114, data regarding angular velocity of the ultrasound imaging device 114, and/or data regarding magnetic force acting on the ultrasound imaging device 114 (which, due to the magnetic field of the earth, may be indicative of orientation relative to the earth). The motion and/or orientation sensor 109 may include an accelerometer, a gyroscope, and/or a magnetometer. Depending on the sensors present in the motion and/or orientation sensor 109, the motion and/or orientation data generated by the motion and/or orientation sensor 109 may describe three degrees of freedom, six degrees of freedom, or nine degrees of freedom for the ultrasound imaging device 114. For example, the motion and/or orientation sensor 109 may include an accelerometer, a gyroscope, and/or magnetometer. Each of these types of sensors may describe three degrees of freedom. If the motion and/or orientation sensor 109 includes one of these sensors, the motion and/or orientation sensor 109 may describe three degrees of freedom. If the motion and/or orientation sensor 109 includes two of these sensors, the motion and/or orientation sensor 109 may describe two degrees of freedom. If the motion and/or orientation sensor 109 includes three of these sensors, the motion and/or orientation sensor 109 may describe nine degrees of freedom. The ultrasound imaging device 114 may transmit motion and/or orientation data to the processing device 102 over a wired (e.g., through a lightning connector or a mini-USB connector) and/or wireless (e.g., using BLUETOOTH, ZIGBEE, and/or WiFi wireless protocols) communication link.

Referring now to the processing device 102, the processor 110 may include specially-programmed and/or special-purpose hardware such as an application-specific integrated circuit (ASIC). For example, the processor 110 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 102 may be configured to process the ultrasound data received from the ultrasound imaging device 114 to generate ultrasound images for display on the display screen 108. The processing may be performed by, for example, the processor 110. The processor 110 may also be adapted to control the acquisition of ultrasound data with the ultrasound imaging device 114. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 102 may be configured to perform certain of the processes described herein using the processor 110 (e.g., one or more computer hardware processors) and one or more articles of manufacture that include non-transitory computer-readable storage media such as the memory 112. The processor 110 may control writing data to and reading data from the memory 112 in any suitable manner. To perform certain of the processes described herein, the processor 110 may execute one or more processor-executable instructions stored in one or more non-transitory computer-readable storage media (e.g., the memory 112), which may serve as non-transitory computer-readable storage media storing processor-executable instructions for execution by the processor 110. The camera 106 may be configured to detect light (e.g., visible light) to form an image. The display screen 108 may be configured to display images and/or videos, and may be, for example, a liquid crystal display (LCD), a plasma display, and/or an organic light emitting diode (OLED) display on the processing device 102. The input device 118 may include one or more devices capable of receiving input from a user and transmitting the input to the processor 110. For example, the input device 118 may include a keyboard, a mouse, a microphone, touch-enabled sensors on the display screen 108, and/or a microphone. The display screen 108, the input device 118, the camera 106, and the speaker 109 may be communicatively coupled to the processor 110 and/or under the control of the processor 110.

It should be appreciated that the processing device 102 may be implemented in any of a variety of ways. For example, the processing device 102 may be implemented as a handheld device such as a mobile smartphone or a tablet. Thereby, a user of the ultrasound imaging device 114 may be able to operate the ultrasound imaging device 114 with one hand and hold the processing device 102 with another hand. In other examples, the processing device 102 may be implemented as a portable device that is not a handheld device, such as a laptop. In yet other examples, the processing device 102 may be implemented as a stationary device such as a desktop computer. The processing device 102 may be connected to the network 116 over a wired connection (e.g., via an Ethernet cable) and/or a wireless connection (e.g., over a WiFi network). The processing device 102 may thereby communicate with (e.g., transmit data to) the one or more servers 134 over the network 116. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application).

FIG. 1 should be understood to be non-limiting. For example, the ultrasound system 100 may include fewer or more components than shown and the processing device 102 may include fewer or more components than shown.

Figure 2:
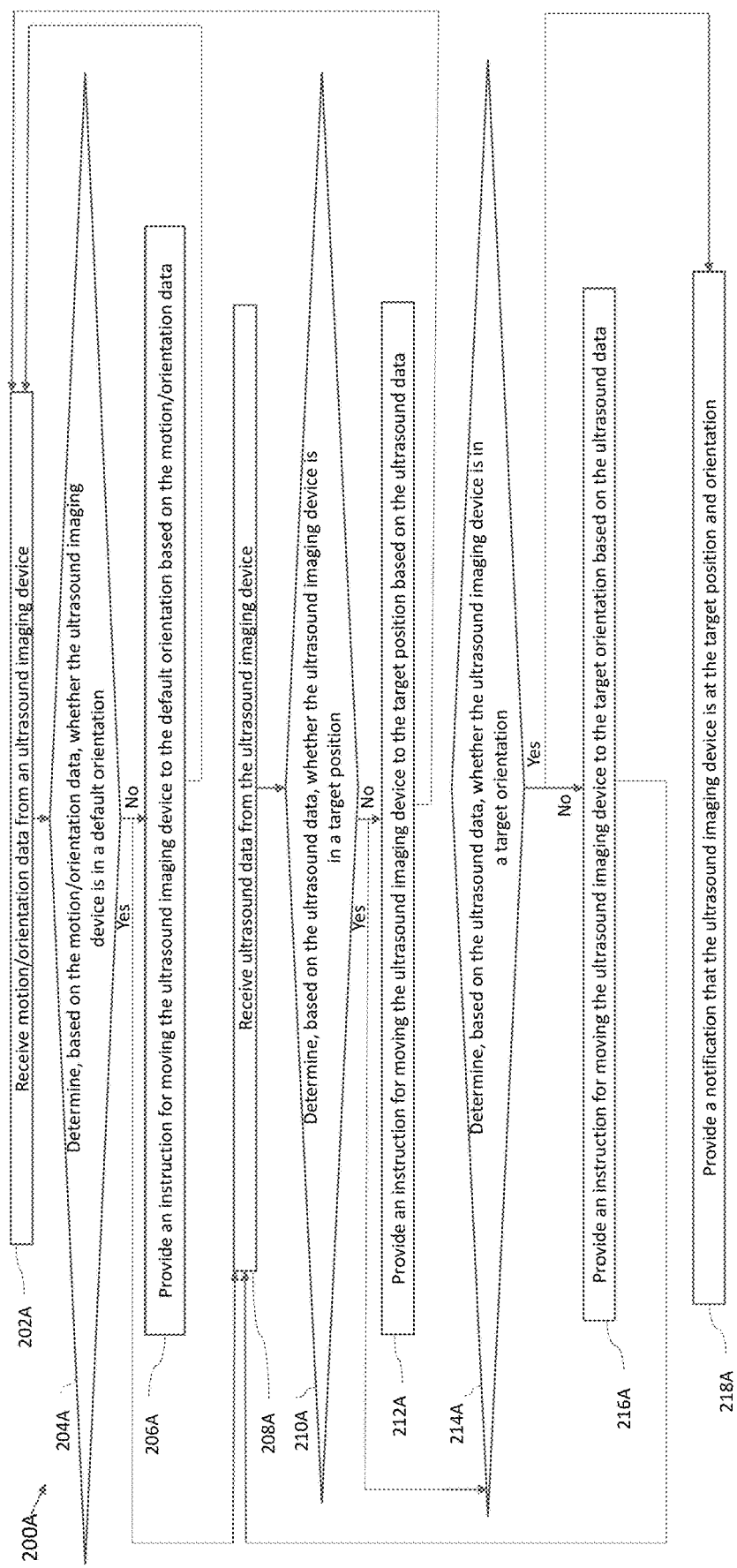
FIG. 2 illustrates an example process for guiding collection of ultrasound data, in accordance with certain embodiments described herein.

FIG. 2 illustrates an example process 200A for guiding collection of ultrasound data, in accordance with certain embodiments described herein. The process 200A includes providing instructions for tilting and/or rotating the ultrasound imaging device to a default orientation, and then providing instructions for translating the ultrasound imaging device to a target position, and then providing instructions for tilting and/or rotating the ultrasound imaging device to a target orientation.

According to an embodiment of the application, a user of an ultrasound imaging device may be guided to move the ultrasound imaging device to a target position and target orientation relative to a subject at which the ultrasound imaging device can collect a target anatomical view (e.g., a parasternal long axis view of the heart). To guide the user, a processing device may be used. The processing device may use a statistical model configured to accept, as an input, ultrasound data collected by the ultrasound imaging device at a current position and orientation relative to the subject, and output one or more instructions for moving the ultrasound imaging device from the current position and orientation to the target position and orientation based on the ultrasound data. The statistical model may continuously output instructions in real-time as the user moves the ultrasound imaging device, based on ultrasound data collected in real-time. The statistical model may be trained on sets of data where each set of data includes ultrasound data collected at a particular position and orientation relative to a subject and a label including an instruction for moving the ultrasound imaging device from the particular position and orientation to the target position and orientation. Because a user may move the ultrasound imaging device to a variety of combinations of positions and orientations, it may be necessary to train the statistical model with ultrasound data collected from a variety of combinations of positions and orientations and associated labels. In other words, the statistical model may need to be trained on ultrasound data collected across the position dimension and the orientation dimension.

The inventors have recognized that it may be helpful for the processing device to provide instructions for tilting and/or rotating the ultrasound imaging device to a default orientation, then to provide instructions (using a statistical model) for translating the ultrasound imaging device to the target position while the ultrasound imaging device is maintained at the default orientation, and then to provide instructions (using the statistical model) for tilting and/or rotating the ultrasound imaging device to the target orientation while the ultrasound imaging device is maintained at the target position. In other words, the statistical model may only need to provide instructions for translating the ultrasound imaging device to the target position when the ultrasound imaging device is at the default orientation, and may only need to provide instructions for tilting and/or rotating the ultrasound imaging device to the target orientation when the ultrasound imaging device is at the target position. Therefore, in contrast to training a statistical model using training ultrasound data collected by ultrasound imaging devices at a variety of combinations of orientations and positions, it may only be necessary to train the statistical model to provide instructions for translating the ultrasound imaging device to the target position and orientation using training ultrasound data collected by ultrasound imaging devices at (1) a variety of positions but at the single default orientation and (2) a variety of orientations but at the single target position. In other words, the dimensionality of the ultrasound data analyzed by the statistical model may be reduced. The ultrasound training data collected by the ultrasound imaging devices at a variety of positions but at the single, default orientation may be helpful for training the statistical model to provide instructions for translating the ultrasound imaging device to the target position when the ultrasound imaging device is at the default orientation. The training data collected by the ultrasound imaging devices at a variety of orientations but at the single target position may be helpful for training the deep learning mode to provide instructions for tilting and/or rotating the ultrasound imaging device to the target orientation when the ultrasound imaging device is at the target position.

In short, the process described above, and described in detail below as process 200A, generally comprises: 1. Providing instructions for moving the ultrasound imaging device to the default orientation (act 202A, 204A, and 206A) 2. Providing instructions for moving the ultrasound imaging device to the target position while maintaining the ultrasound imaging device at the default orientation (act 208A, 210A, and 212A) and 3. Providing instructions for moving the ultrasound imaging device to the target orientation at the target position (act 214A and 216A). In other words, instructions for moving the ultrasound imaging device to the target position may be provided before providing any instructions for moving the ultrasound imaging device to the target orientation. The process 200A may be performed by a processing device (e.g., processing device 102) in an ultrasound system (e.g., ultrasound system 100). The processing device may be, for example, a mobile phone, tablet, laptop, or server, and may be in operative communication with an ultrasound imaging device (e.g., ultrasound imaging device 114).

In act 202A of process 200A, the processing device receives motion and/or orientation data from the ultrasound imaging device. For example, the motion and/or orientation data may include data regarding acceleration of the object, data regarding angular velocity of the object, and/or data regarding magnetic force acting on the object (which, due to the magnetic field of the earth, may be indicative of orientation relative to the earth). The ultrasound imaging device may include an accelerometer, a gyroscope, and/or a magnetometer, and these devices may be used by the ultrasound imaging device to generate the motion and/or orientation data. Depending on the devices used to generate the motion and/or orientation data, the motion and/or orientation data may describe three degrees of freedom, six degrees of freedom, or nine degrees of freedom for the ultrasound imaging device. The ultrasound imaging device may transmit the motion and/or orientation data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 200A proceeds from act 202A to act 204A.

In act 204A, the processing device determines, based on the motion and/or orientation data received in act 202A, whether the ultrasound imaging device is in a default orientation (i.e., tilt and rotation). For an example of a default orientation, see FIGS. 5-6. The processing device may determine the current orientation of the ultrasound imaging device based on the motion and/or orientation data, compare the current orientation to the default orientation, and determine whether there are differences between the current orientation and the default orientation. If the processing device determines that there are differences between the current orientation and the default orientation (i.e., the ultrasound imaging device is not in the default orientation), the process 200A proceeds from act 204A to act 206A. If the processing device determines that there is no difference between the current orientation and the default orientation (i.e., the ultrasound imaging device is in the default orientation), the process 200A proceeds from act 204A to act 208A.

Act 206A occurs if the processing device determines at act 204A that the ultrasound imaging device is not in the default orientation. In act 206A, the processing device provides an instruction for moving the ultrasound imaging device to the default orientation based on the motion and/or orientation data received in act 202A. For example, based on the differences between the current orientation and the default orientation of the ultrasound imaging device, the processing device may determine instructions for eliminating those differences (e.g., tilting or rotating the ultrasound imaging device). To provide the instruction for moving the ultrasound imaging device to the default orientation, the processing device may display the instruction on a display screen (e.g., display screen 108) of the processing device. For example, if the processing device is a smartphone coupled to the ultrasound imaging device by a cable, the smartphone may display the instruction on its display screen. The displayed instruction may include any combination of words (e.g., "Rotate the probe clockwise") and directional indicators. The processing device may display directional indicators on an image of the ultrasound imaging device and/or the subject. In some embodiments, the processing device may receive or capture a real-time video of the ultrasound imaging device and/or the subject and display directional indicators superimposed on the video of the ultrasound imaging device and/or the subject in real-time, where the direction of the directional indicators indicates the direction in which the ultrasound imaging device should be moved relative to the subject. This may be considered an augmented reality display. In some embodiments, the processing device may generate audio containing the instructions from speakers (e.g., speakers included in the processing device).

The process 200A then proceeds back to act 202A, in which the processing device receives motion and/or orientation data from the ultrasound imaging device. This motion and/or orientation data may be from the ultrasound imaging device after the user has moved the ultrasound imaging device in response to the instruction provided by the processing device in act 206A. Act 202A, act 204A, and optionally act 206A may proceed repeatedly or iteratively (namely, the processing device may receive motion and/or orientation data, determine based on the motion and/or orientation data whether the ultrasound imaging device is in the default orientation, and if not, provide an instruction for moving the ultrasound imaging device to the default orientation) until the processing device determines that the ultrasound imaging device is in the default orientation and proceeds to act 208A. It should be noted that multiple movements (e.g., one or more tilts and one or more rotations) may be necessary to move the ultrasound imaging device to the default orientation, and the processing device may provide instructions to do one of these movements at each iteration through act 202A, act 204A, and act 206A.

Act 208A occurs if the processing device determines at act 204A that the ultrasound imaging device is in the default orientation. In act 208A, the processing device receives ultrasound data collected by the ultrasound imaging device. The ultrasound data may include, for example, raw acoustical data, scan lines generated from raw acoustical data, or ultrasound images generated from raw acoustical data. In some embodiments, the ultrasound imaging device may generate scan lines and/or ultrasound images from raw acoustical data and transmit the scan lines and/or ultrasound images to the processing device. In other embodiments, the ultrasound imaging device may transmit the raw acoustical data to the processing device and the processing device may generate the scan lines and/or ultrasound images from the raw acoustical data. In still other embodiments, the ultrasound imaging device may generate scan lines from the raw acoustical data, transmit the scan lines to the processing device, and the processing device may generate ultrasound images from the scan lines. The ultrasound imaging device may transmit the ultrasound data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 200A proceeds from act 208A to act 210A.

In act 210A, the processing device determines, based on the ultrasound data received in act 208A, whether the ultrasound imaging device is at a target position. If the processing device determines at act 210A that the ultrasound imaging device is at the target position, the process 200A proceeds from act 210A to act 214A. If the processing device determines that the ultrasound imaging device is not at the target position, the process 200A proceeds from act 210A to act 212A. In act 212A, the processing device provides an instruction for moving the ultrasound imaging device to the target position based on the ultrasound data received in act 208A. As described above, in some embodiments, the processing device may input the ultrasound data to a statistical model (e.g., a convolutional neural network or other deep learning statistical model) configured to accept ultrasound data, determine whether the ultrasound imaging device is at the target position and orientation based on the ultrasound data collected at the target position, and if not, output an instruction for moving the ultrasound imaging device to the target position orientation based on the ultrasound data. The statistical model may be a convolutional neural network, a fully connected neural network, a recurrent neural network (e.g., a long short-term memory (LSTM) recurrent neural network), a random forest, a support vector machine, a linear classifier, and/or any other statistical model. Further description of statistical models may be found with reference to FIG. 8. The target position and orientation of the ultrasound imaging device may be a position and orientation of the ultrasound imaging device relative to a subject such that the ultrasound imaging device can collect a target anatomical view (e.g., a parasternal long axis view of the heart).

As described above, at acts 202A, 204A, and 206A, the processing device provides instructions for moving the ultrasound imaging device to a default orientation. Accordingly, at act 208A, act 210A, and act 212A, the ultrasound imaging device may be at the default orientation. As further described above, it may be helpful for the statistical model to provide instructions for moving the ultrasound imaging device to the target position while the ultrasound imaging device is maintained at the default orientation. Therefore, at act 212A, when the processing device provides an instruction for moving the ultrasound imaging device to the target position, the processing device may only provide an instruction including translation, but not tilting or rotation, such that the ultrasound imaging device may be maintained at the default orientation. In particular, the device may generally be configured to provide, or capable of providing, instructions for translation, tilting, and rotation based on the statistical model, but in the scenario in which the default orientation is already achieved, subsequent instructions for moving the ultrasound device to a target position may be ordered such that instructions for translation are provided until a target location of the ultrasound device is achieved, and subsequently instructions for rotation and/or tilting are provided. While moving the ultrasound device to the target location, instructions regarding orientation may be suppressed, and once the target location is achieved, instructions regarding translation may not be needed and/or may be suppressed. Other ordering of instructions for translation, rotation, and tilting may be used in other embodiments.

In some embodiments, the statistical model may be configured, for example through training, to accept ultrasound data and output an instruction for moving the ultrasound imaging device to a target position based on the ultrasound data. In particular, the statistical model may be trained on sets of training data, where each set of training data includes ultrasound data collected with an ultrasound imaging device at a particular position and a label indicating an instruction for moving the ultrasound imaging device from the particular position to the target position. The training data may be labeled manually by an annotator (e.g., a doctor, sonographer, or other medical professional). The statistical model may thereby learn what instruction to provide based on inputted ultrasound data. As further described above, because the ultrasound imaging device should be at the default orientation at acts 208A, 210A, and 212A, the training data may only need to include training data from ultrasound imaging devices with varying positions at the default orientation.

In some embodiments, the statistical model may be stored in memory on the processing device and accessed internally by the processing device. In other embodiments, the statistical model may be stored in memory on another device, such as a remote server, and the processing device may transmit the ultrasound data to the external device which is configured to input the ultrasound data to the statistical model and transmit the instruction outputted by the statistical model back to the processing device. Transmission between the processing device and the external device may be over a wired communication link (e.g., over Ethernet, a Universal Serial Bus (USB) cable or a Lightning cable) or over a wireless communication link (e.g., over a BLUETOOTH, WiFi, or ZIGBEE wireless communication link)

To provide the instruction for moving the ultrasound imaging device to the target position, the processing device may display the instruction on a display screen (e.g., display screen 108) of the processing device. For example, if the processing device is housed in a smartphone coupled to the ultrasound imaging device by a cable, the processing device may display the instruction on the display screen on the smartphone. The displayed instruction may include any combination of words (e.g., "Move the probe medially") and directional indicators. The processing device may display directional indicators on an image of a subject (e.g., an image of a person) and/or an image of the ultrasound imaging device. In some embodiments, the processing device may receive or capture an image of the subject and/or the ultrasound imaging device and display directional indicators superimposed on the image of the subject and/or the ultrasound imaging device, where the direction of the directional indicators indicates the direction in which the ultrasound imaging device should be moved relative to the subject. This may be considered an augmented reality display. In some embodiments, the processing device may generate audio containing the instructions from speakers (e.g., speakers included in the processing device).

The process 200A then proceeds from act 212A back to act 202A, act 204A, and optionally act 206A, namely, the processing device receives motion and/or orientation data, determines based on the motion and/or orientation data whether the ultrasound imaging device is in the default orientation, and if not, the processing device provides an instruction for moving the ultrasound imaging device to the default orientation. Although act 208A, act 210A, and act 212A only proceed if the processing device determines at act 204A that the ultrasound imaging device is at the default orientation, it is possible that the user may move the ultrasound imaging device away from the default orientation (i.e., tilt or rotate the ultrasound imaging device) while moving the ultrasound imaging device in response to the instruction provided by the processing device in act 212A (despite the instruction only including instructions to translate the ultrasound imaging device). Accordingly, after providing the instruction to translate the ultrasound imaging device in act 212A, at act 202A, act 204A, and act 206A, the processing device may determine whether the ultrasound imaging device is still in the default orientation, and if not, provide instructions for moving the ultrasound imaging device back to the default orientation, prior to proceeding to act 208A, act 210A, and optionally act 212A.

Acts 208A, 210A, and 212A may proceed repeatedly (namely, the processing device may receive ultrasound data, determine based on the ultrasound data whether the ultrasound imaging device is in the target position, and if not, provide an instruction for moving the ultrasound imaging device to the target position) until the processing device determines that the ultrasound imaging device is in the target position. It should be noted that multiple movements (e.g., translations in different directions) may be necessary to move the ultrasound imaging device to the target position, and the processing device may provide instructions to do one of these movements through each iteration through acts 208A, 210A, and 212A.

Act 214A occurs if the processing device determines at act 210A that the ultrasound imaging device is at the target position. Once the ultrasound imaging device is at the target position, it may be necessary for the ultrasound imaging device to be moved further to a target orientation at the target position in order to collect the target anatomical view. In act 214A, the processing device determines, based on the ultrasound data received in act 208A (or, in some embodiments, new ultrasound data received since act 208A), whether the ultrasound imaging device is in the target orientation (i.e., tilt and orientation). If the processing device determines that the ultrasound imaging device is in the target orientation, the process 200A proceeds from act 214A to act 218A. If the processing device determines that the ultrasound imaging device is not in the target orientation, the process 200A proceeds from act 214A to act 216A. In act 216A, the processing device provides an instruction for moving the ultrasound imaging device to the target orientation based on the ultrasound data received in act 208A (or, in some embodiments, new ultrasound data received since act 208A). As described above, in some embodiments, the processing device may input the ultrasound data to the statistical model described with reference to acts 210A and 212A that is configured to accept ultrasound data, determine whether the ultrasound imaging device is at the target position and orientation based on the ultrasound data collected at the target position, and if not, output an instruction for moving the ultrasound imaging device to the target position orientation based on the ultrasound data. At acts 208A, 210A, and 212A, the processing device provides instructions for moving the ultrasound imaging device to the target position. Accordingly, at act 214A and act 216A, the ultrasound imaging device may be at the default target position. As further described above, it may be helpful for the statistical model to provide instructions for moving the ultrasound imaging device to the target orientation while the ultrasound imaging device is maintained at the target orientation.

Therefore, at act 216A, when the processing device provides an instruction for moving the ultrasound imaging device to the target position, the processing device may only provide an instruction including tilting and rotation, but not translation, such that the ultrasound imaging device may be maintained at the target rotation. In particular, the statistical model may output instructions including translation, rotation, and/or tilting, but the processing device may only output instructions for tilting and/or rotation and suppress (e.g., not output) any instructions for translation.

In some embodiments, the statistical model may be configured through training to accept ultrasound data and output an instruction for moving the ultrasound imaging device to a target orientation based on the ultrasound data. In particular, the statistical model may be trained on sets of training data, where each set of training data includes ultrasound data collected with an ultrasound imaging device at a particular orientation and a label indicating an instruction for moving the ultrasound imaging device from the particular orientation to the target orientation. The training data may be labeled manually by an annotator (e.g., a doctor, sonographer, or other medical professional). The statistical model may thereby learn what instruction to provide based on inputted ultrasound data. As further described above, because the ultrasound imaging device should be at the target position at acts 214A and 216A, the training data may only need to include training data from ultrasound imaging devices with varying orientations at the target position.

To provide the instruction for moving the ultrasound imaging device to the target orientation, the processing device may display the instruction on a display screen (e.g., display screen 108) of the processing device. For example, if the processing device is housed in a smartphone coupled to the ultrasound imaging device by a cable, the processing device may display the instruction on the display screen on the smartphone. The displayed instruction may include any combination of words (e.g., "Rotate the probe clockwise") and directional indicators. The processing device may display directional indicators on an image of a subject (e.g., an image of a person) and/or the ultrasound imaging device. In some embodiments, the processing device may receive or capture a real-time video of the ultrasound imaging device and/or the subject and display directional indicators superimposed on the video of the ultrasound imaging device and/or the subject in real-time, where the direction of the directional indicators indicates the direction in which the ultrasound imaging device should be moved relative to the subject. This may be considered an augmented reality display. In some embodiments, the ultrasound imaging device may generate audio containing the instructions from speakers (e.g., speakers included in the processing device).

The process 200A then proceeds from act 216A back to act 208A, act 210A, and optionally act 212A, namely, the processing device receives ultrasound data, determines based on the ultrasound data whether the ultrasound imaging device is at the target position, and if not, the processing device provides an instruction for moving the ultrasound imaging device to the target position. Although act 214A and act 216A only proceed if the processing device determines at act 210A that the ultrasound imaging device is at the target position, it is possible that the user may move the ultrasound imaging device away from the target position (i.e., translate the ultrasound imaging device) while moving the ultrasound imaging device in response to the instruction provided by the processing device in act 216A (despite the instruction only including instructions to rotate and/or tilt the ultrasound imaging device). Accordingly, after providing the instruction to tilt and/or rotate the ultrasound imaging device in act 216A, at act 208A, act 210A, and act 212A, the processing device may determine whether the ultrasound imaging device is still at the target position, and if not, provide instructions for moving the ultrasound imaging device back to the target position, prior to proceeding to act 214A and optionally act 216A.

Acts 214A and 216A may proceed repeatedly (namely, the processing device may receive ultrasound data, determine based on the ultrasound data whether the ultrasound imaging device is in the target orientation, and if not, provide an instruction for moving the ultrasound imaging device to the target orientation) until the processing device determines that the ultrasound imaging device is in the target orientation. It should be noted that multiple movements (e.g., tilts and/or rotations) may be necessary to move the ultrasound imaging device to the target position, and the processing device may provide instructions to do one of these movements through each iteration through acts 214A and 216A.

Act 218A occurs if the processing device determines at act 214A that the processing device is at the target orientation. In act 218A, the processing device provides a notification that the ultrasound imaging device is at the target position and orientation. To provide the notification, the processing device may display the notification on a display screen (e.g., display screen 108) of the processing device. For example, if the processing device is housed in a smartphone coupled to the ultrasound imaging device by a cable, the processing device may display the instruction on the display screen on the smartphone. The displayed instruction may include any combination of words (e.g., "Correct") and symbols (e.g., a checkmark). In some embodiments, the ultrasound imaging device may generate audio containing the notification from speakers (e.g., speakers included in the processing device).

As described above, the inventors have recognized that it may be possible for a processing device to guide a user of an ultrasound imaging device to move the ultrasound imaging device to a target position and target orientation relative to a subject at which the ultrasound imaging device can collect a target anatomical view (e.g., a parasternal long axis view of the heart). To guide the user, the processing device may output one or more instructions for moving the ultrasound imaging device from the current position and orientation to the target position and orientation. To output an instruction, the processing device may capture, using a camera (e.g., camera 106), a video in real-time of the ultrasound imaging device and/or the subject, and display an augmented reality display including a directional indicator (e.g., an arrow) superimposed on the video, where the directional indicator indicates the instruction for moving the ultrasound imaging device. For example, if the instruction is to move the ultrasound imaging device in the superior direction (i.e., in the superior direction relative to the subject), the processing device may display a directional indicator in the superior direction.

Figure 3:
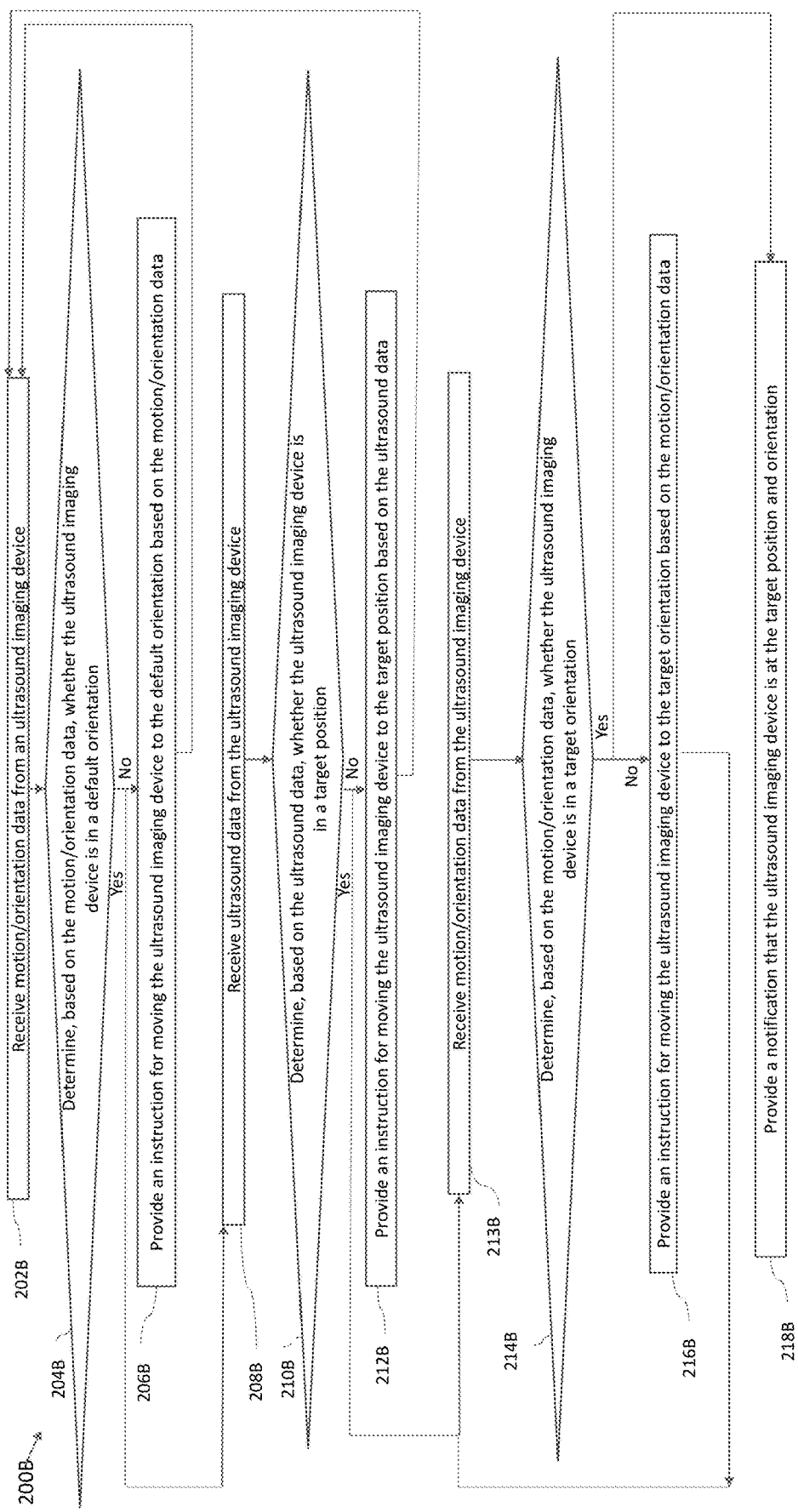
FIG. 3 illustrates another example process for guiding collection of ultrasound data, in accordance with certain embodiments described herein.

FIG. 3 illustrates another example process 200B for guiding collection of ultrasound data, in accordance with certain embodiments described herein. Generally, the process 200B differs from the process 200A in that the processing device determines whether the ultrasound imaging device is in the default orientation based on motion and/or orientation data, and the processing device provides an instruction for rotating and/or tilting the ultrasound imaging to the default orientation based on the motion and/or orientation data. The process 200A makes the determination and provides the instruction based on ultrasound data.

As an example of the process 200B, to provide instructions for moving the ultrasound imaging device to a first anatomical view (e.g., a parasternal long axis view of the heart), the processing device may first provide instructions to rotate and/or tilt the ultrasound imaging device to the default orientation, then provide instructions to translate the ultrasound imaging device to a target position specific to the first anatomical view, and then provide instructions to rotate and/or tilt the ultrasound imaging device to a target orientation specific to the first anatomical view. To provide instructions for moving the ultrasound imaging device to a second anatomical view (e.g., an apical four-chamber view of the heart), the processing device may first provide instructions to rotate and/or tilt the ultrasound imaging device to the default orientation, then provide instructions to translate the ultrasound imaging device to a target position specific to the second anatomical view, and then provide instructions to rotate and/or tilt the ultrasound imaging device to a target orientation specific to the second anatomical view. Accordingly, translation should only occur when the ultrasound imaging device is at the default orientation. Thus, to collect training data for training a deep learning model that outputs the translation instructions, it may be only be necessary to collect data from ultrasound imaging devices when the ultrasound imaging devices are at the default orientation. Such training data may be used for training the deep learning model to output translation instructions both for the first anatomical view and the second anatomical view.

Acts 202B-212B and 218B are the same as acts 202A-212A and 218A, respectively (meaning 202A is the same as 202B, 204A is the same as 204B, 206A is the same as 206B, 208A is the same as 208B, etc.), except that at 210B, if the processing device determines that the ultrasound imaging device is in the target position, the process 200B proceeds to act 213B. At act 213B, the processing device receives motion and/or orientation data from the ultrasound imaging device, as in act 202B. The process 200B proceeds from act 213B to act 214B. Aside from differences described herein between the process 200A and the process 200B, any other aspects of the process 200A may apply to the process 200B.

In act 214B, the processing device determines, based on the motion and/or orientation data received in act 213B, whether the ultrasound imaging device is in the target orientation. In some embodiments, the target orientation may be selected as the orientation that the ultrasound imaging device must be in relative to gravity to collect the target anatomical view when a typical subject (e.g., typical across the general human population or a subset thereof) is positioned in some default orientation relative to gravity (such as lying on his/her right side, on his/her left side, or on his/her back). In such embodiments, the target orientation may be defined in terms of motion and/or orientation data and the processing device may, at act 214B, determine whether the ultrasound imaging device is in the target orientation based on the motion and/or orientation data received in act 213B (similarly to how the processing device determines whether the ultrasound imaging device is in the default orientation based on motion and/or orientation data in act 204B). If the processing device determines at act 214B that the ultrasound imaging device is in the target orientation, the process 200B proceeds from act 214B to act 218B, where the processing device provides a notification that the ultrasound imaging device is at the target position and orientation. If the processing device determines at act 214B that the ultrasound imaging device is not in the target orientation, the process 200B proceeds from act 214B to act 216B.

In act 216B, the processing device provides an instruction for moving the ultrasound imaging device to the target orientation based on the motion and/or orientation data similarly to how the processing device provides an instruction for moving the ultrasound imaging device to the default orientation in act 206B. The process 200B proceeds from act 216B back to act 213B, act 214B, and optionally act 216B, namely, the processing device receives motion and/or orientation data, determines based on the motion and/or orientation data whether the ultrasound imaging device is at the target orientation, and if not, the processing device provides an instruction for moving the ultrasound imaging device to the target orientation.

Figure 4:
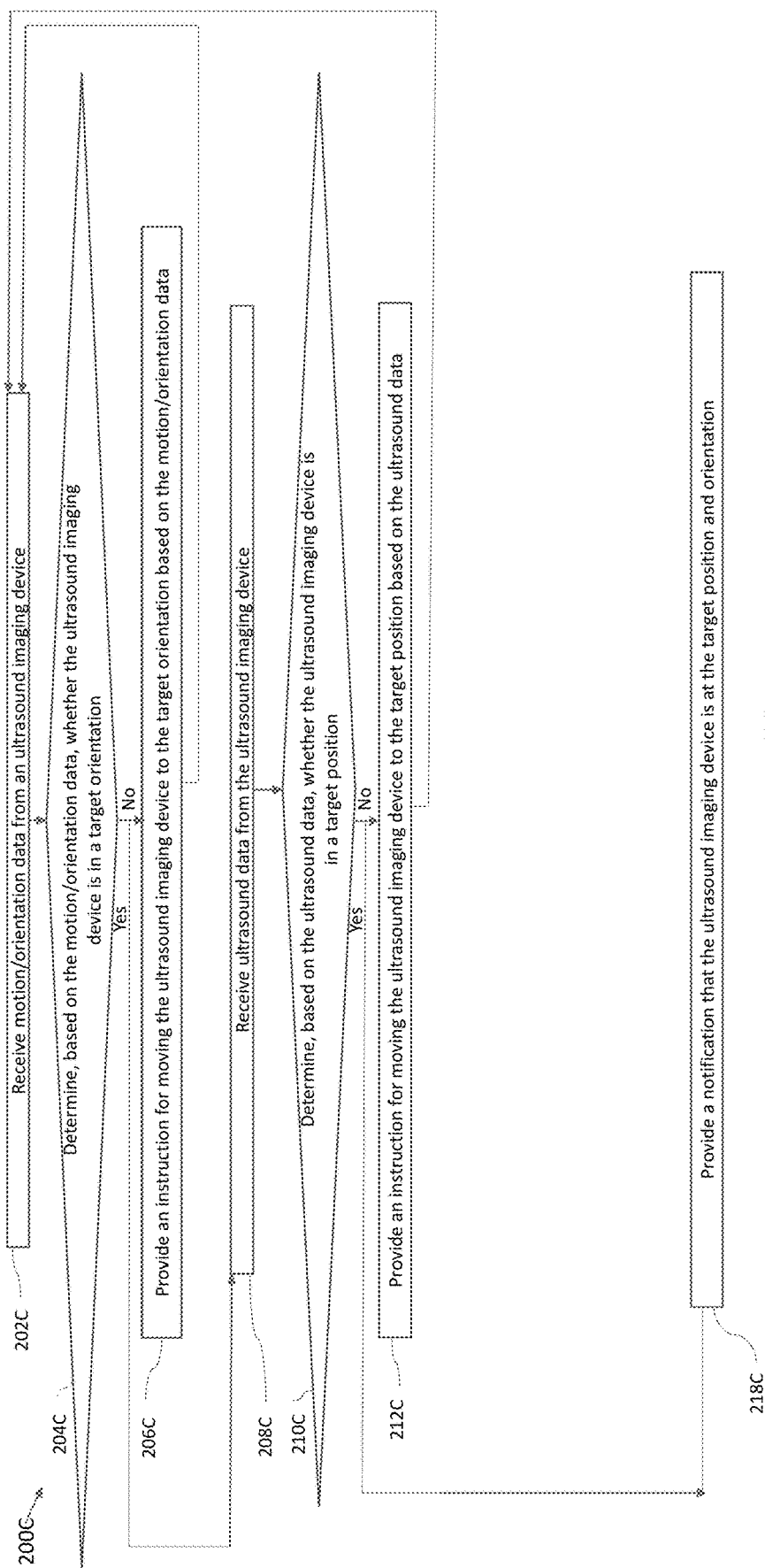
FIG. 4 illustrates another example process for guiding collection of ultrasound data, in accordance with certain embodiments described herein.

FIG. 4 illustrates another example process 200C for guiding collection of ultrasound data, in accordance with certain embodiments described herein. Generally, the process 200C differs from the process 200B in that the processing device initially determines whether the ultrasound imaging device is at a target orientation (rather than a default orientation) based on motion and/or ultrasound data and provides instructions for rotating and/or tilting the ultrasound imaging device to the target orientation based on the motion and/or ultrasound data.

As an example of the process 200C, to provide instructions for moving the ultrasound imaging device to a first anatomical view (e.g., a parasternal long axis view of the heart), the processing device may first provide instructions to rotate and/or tilt the ultrasound imaging device to a target orientation specific to the first anatomical view and then provide instructions to translate the ultrasound imaging device to a target position specific to the first anatomical view. To provide instructions for moving the ultrasound imaging device to a second anatomical view (e.g., an apical four-chamber view of the heart), the processing device may first provide instructions to rotate and/or tilt the ultrasound imaging device to a target orientation specific to the second anatomical view and then provide instructions to translate the ultrasound imaging device to a target position specific to the second anatomical view. Thus, the process 200C eliminates the steps in the process 200B of rotating and/or tilting the ultrasound imaging device to a default orientation. However, because translation may occur when the ultrasound imaging device is in an orientation specific to the first anatomical view or an orientation specific to the second anatomical view, it may be necessary to collect one set of training data for training a deep learning model that outputs translation instructions from ultrasound imaging devices that are at the orientation specific to the first anatomical view, and another set of training data for training the deep learning model from ultrasound imaging devices that are at the orientation specific to the second anatomical view.

Acts 202C-212C are the same as acts 202B-212B, with the exception that in act 204C, the processing device determines whether the ultrasound imaging device is at a target (rather than default) orientation, and in act 206C, the processing device provides an instruction for moving the ultrasound imaging device to the target (rather than default) orientation. As described above, in some embodiments, the target orientation may be selected as the orientation that the ultrasound imaging device must be in relative to gravity to collect the target anatomical view when a typical subject (e.g., typical across the general human population or a subset thereof) is positioned in some default orientation relative to gravity (such as lying on his/her right side, on his/her left side, or on his/her back). In such embodiments, the target orientation may be defined in terms of motion and/or orientation data. As further differences between the process 200C and the process 200B, if in act 210C, the processing device determines that the ultrasound imaging device is in the target position, the processing device proceeds from act 210C to act 218C, where the processing device provides a notification that the ultrasound imaging device is at the target position and orientation. Additionally, the process 200C lacks equivalents of steps 213B-216B that occur between the acts 212C and 218C. Aside from differences described herein between the process 200C and the process 200B, any other aspects of the process 200B may apply to the process 200C.

Figure 5:
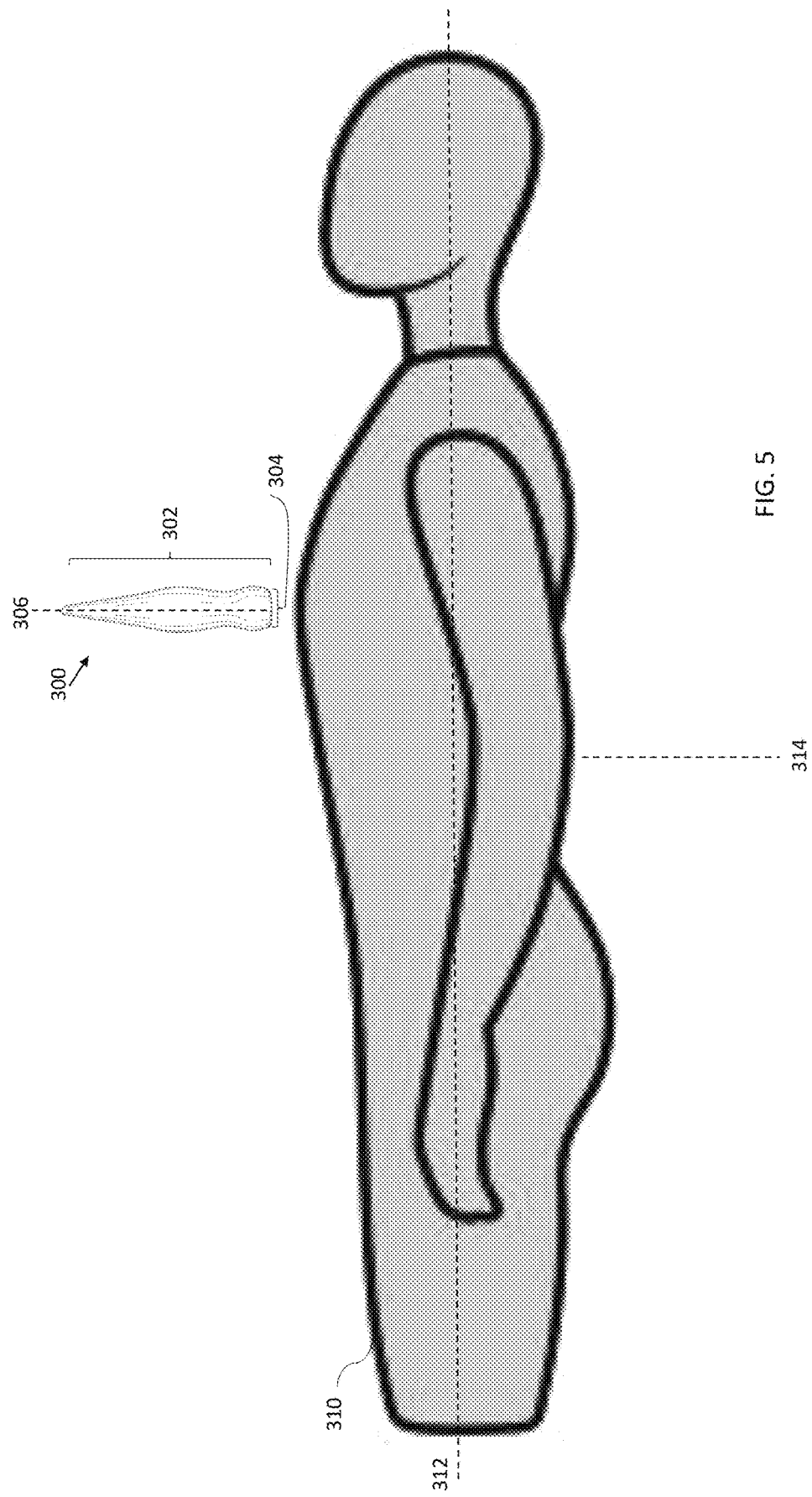
FIG. 5 illustrates an example default orientation for an ultrasound imaging device relative to a subject being imaged, where the subject is shown from the side, in accordance with certain embodiments described herein.
Figure 6:
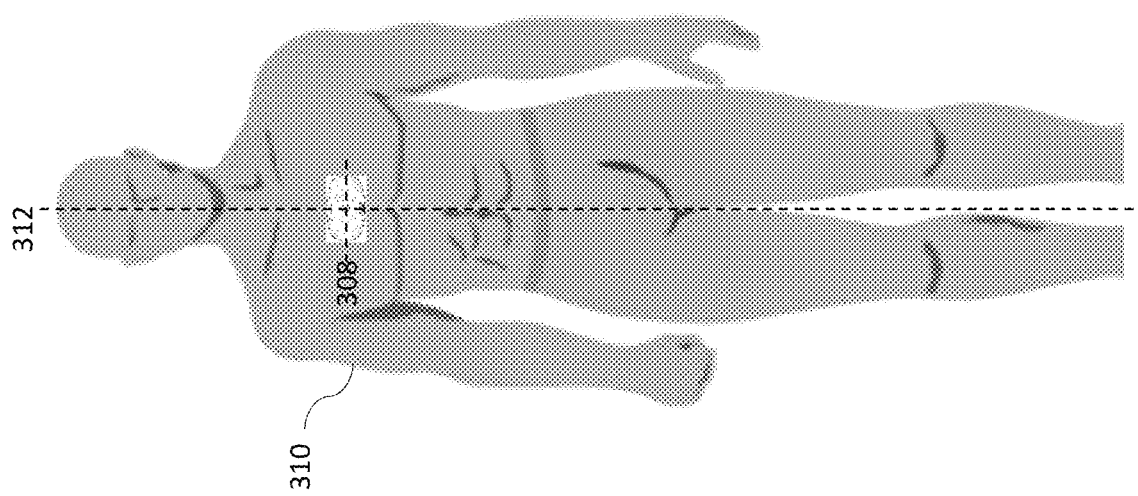
FIG. 6 illustrates the default orientation of the ultrasound imaging device of FIG. 5, where the subject is shown from the top.

FIG. 5 illustrates an example default orientation for an ultrasound imaging device 300 relative to a subject 310 being imaged, where the subject 310 is shown from the side, in accordance with certain embodiments described herein. FIG. 6 illustrates the default orientation of FIG. 5, where the subject 310 is shown from the top. The ultrasound imaging device 300 includes a body 302 and a sensor 304. The body 302 of the ultrasound imaging device 300 has a longitudinal axis 306 and the sensor 304 of the ultrasound imaging device 300 has a longitudinal axis 308. The subject 310 has a longitudinal axis 312. FIGS. 5-6 also show an axis of gravity 314. The default orientation is when the longitudinal axis 306 of the body 302 of the ultrasound imaging device 300 is parallel to the axis of gravity 314 and the longitudinal axis 308 of the sensor 304 of the ultrasound imaging device 300 is perpendicular to the longitudinal axis 312 of the subject 310 being imaged. The subject 310 may be positioned in some default orientation relative to gravity, such as lying on his/her right side, on his/her left side, or on his/her back, such that the ultrasound imaging device 300 may sense (using motion and/or orientation sensors) when the ultrasound imaging device 300 is perpendicular to the longitudinal axis 312 of the subject 310 being imaged. The longitudinal axis 308 of the sensor 304 of the ultrasound imaging device 300 is not visible in FIG. 5 as the longitudinal axis 308 is normal to the figure (i.e., goes into and out of the page). It should be appreciated that the longitudinal axis 306 of the body 302 of the ultrasound imaging device 300 and the longitudinal axis 308 of the sensor 304 of the ultrasound imaging device 300 are constructs for describing a default orientation, but other default orientations not related to the longitudinal axis 306 of the body 302 of the ultrasound imaging device 300 and/or the longitudinal axis 308 of the sensor 304 of the ultrasound imaging device 300 are possible. Indeed, the body 302 and/or the sensor 304 of the ultrasound imaging device 300 may be shaped such that they do not have a clearly defined longitudinal axis. Other default orientations may be possible.

Figure 7:
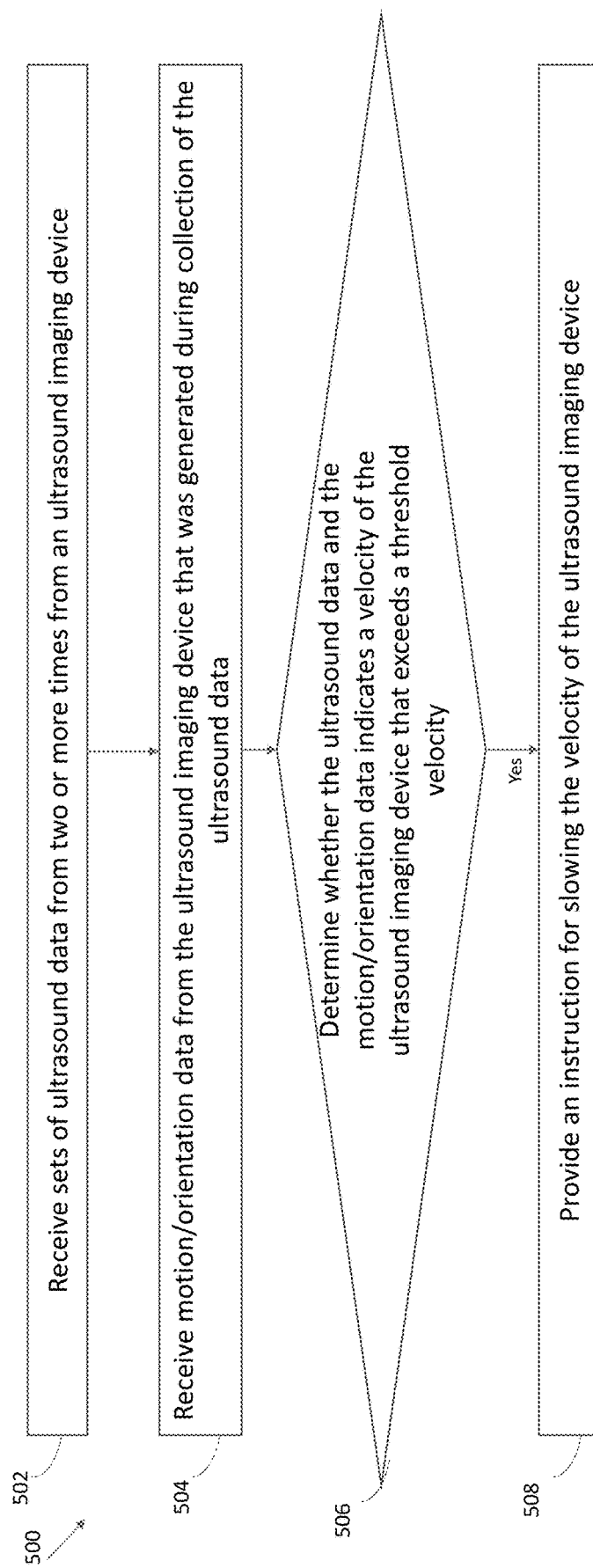
FIG. 7 illustrates an example process for guiding collection ultrasound data by determining whether ultrasound imaging device exceeds a threshold velocity, in accordance with certain embodiments described herein.

FIG. 7 illustrates an example process 500 for guiding collection of ultrasound data by determining whether the ultrasound imaging device exceeds a threshold velocity, in accordance with certain embodiments described herein. The process 500 may be performed by a processing device (e.g., processing device 102) in an ultrasound system (e.g., ultrasound system 100). The processing device may be, for example, a mobile phone, tablet, laptop, or server, and may be in operative communication with an ultrasound imaging device (e.g., ultrasound imaging device 114).

In act 502, the processing devices receives sets of ultrasound data from two or more times from an ultrasound imaging device. For example, the ultrasound data may include a set of ultrasound data collected at one time from one location on a subject and a set of ultrasound data collected at a later time from another location on a subject. The ultrasound data may include, for example, raw acoustical data, scan lines generated from raw acoustical data, or ultrasound images generated from raw acoustical data. In some embodiments, the ultrasound imaging device may generate scan lines and/or ultrasound images from raw acoustical data and transmit the scan lines and/or ultrasound images to the processing device. In other embodiments, the ultrasound imaging device may transmit the raw acoustical data to the processing device and the processing device may generate the scan lines and/or ultrasound images from the raw acoustical data. In still other embodiments, the ultrasound imaging device may generate scan lines from the raw acoustical data, transmit the scan lines to the processing device, and the processing device may generate ultrasound images from the scan lines. The ultrasound imaging device may transmit the ultrasound data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 500 proceeds from act 502 to act 504.

In act 504, the processing device receives motion and/or orientation data from the ultrasound imaging device that was generated during collection of the ultrasound data in act 502. For example, the motion and/or orientation data may include data regarding acceleration of the object, data regarding angular velocity of the object, and/or data regarding magnetic force acting on the object (which, due to the magnetic field of the earth, may be indicative of orientation relative to the earth). The ultrasound imaging device may include an accelerometer, a gyroscope, and/or a magnetometer, and these devices may be used by the ultrasound imaging device to generate the motion and/or orientation data. Depending on the devices used to generate the motion and/or orientation data, the motion and/or orientation data may describe three degrees of freedom, six degrees of freedom, or nine degrees of freedom for the ultrasound imaging device. The ultrasound imaging device may transmit the motion and/or orientation data over a wired communication link (e.g., over Ethernet, a Universal Serial Bus (USB) cable or a Lightning cable) or over a wireless communication link (e.g., over a BLUETOOTH, WiFi, or ZIGBEE wireless communication link) to the processing device. The process 500 proceeds from act 504 to act 506.

In act 506, the processing device determines whether the ultrasound data received in act 502 and the motion and/or orientation data received in act 504 indicates a velocity of the ultrasound imaging device that exceeds a threshold velocity. If the processing device determines that the velocity of the ultrasound imaging device exceeds the threshold velocity, the process 500 proceeds from act 506 to act 508. In act 508, the processing device provides an instruction to the user for slowing the velocity of the ultrasound imaging device. In some embodiments, the processing device may be configured to access a statistical model configured to accept, as inputs, ultrasound data from two or more times collected by an ultrasound imaging device and motion and/or orientation data for the ultrasound imaging device generated during collection of the ultrasound data, and output a velocity of the ultrasound imaging device. To train the statistical model to determine velocity from ultrasound data, the statistical model may be trained on ultrasound data, each set of which is labeled with the time when the ultrasound data was collected and the position of the ultrasound imaging device when it collected the ultrasound data. The statistical model may be able to determine the velocity of the ultrasound imaging device during collection of two sets of ultrasound data based on differences in the position and time corresponding to each set of ultrasound data. For example, if one set of ultrasound data was collected at position p1 and time t1 and another set of ultrasound data was collected at position p2 and time t2, the statistical model may determine the velocity of the ultrasound imaging device during collection of the two sets of ultrasound data to be (p1−p2)/(t1−t2). In embodiments in which the motion and/or orientation data includes acceleration data for the ultrasound imaging device, the statistical model may be able to determine the velocity of the ultrasound imaging device by integrating the acceleration data. The statistical model may be able to more accurately determine the velocity of the ultrasound imaging device using both ultrasound data and motion and/or orientation data. In some embodiments, the statistical model may determine the velocity of the ultrasound imaging device based only on ultrasound data. In such embodiments, act 504 may be absent. In some embodiments, the statistical model may determine the velocity of the ultrasound imaging device based only on motion and/or orientation data. In such embodiments, act 502 may be absent.

In some embodiments, the processing device may be configured to access another statistical model configured to accept ultrasound data as an input and output an instruction for moving the ultrasound imaging device to a target position and/or orientation based on the ultrasound data. In such embodiments, the processing device may be configured to provide the instruction. The threshold velocity may be related to the lag time between when the ultrasound imaging device collects ultrasound data and when the processing device provides the instruction. In some embodiments, the threshold velocity may be approximately in the range of 0.25 cm/s-2 cm/s, such as 0.25 cm/s, 0.5 cm/s, 0.75 cm/s, 1 cm/s, 1.25 cm/s, 1.5 cm/s, 1.75 cm/s, 2 cm/s, or any other suitable threshold velocity. The inventors have recognized that providing instructions to a user to slow down movement of an ultrasound imaging device when the velocity of the ultrasound imaging device exceeds a threshold velocity may be helpful in providing more accurate instructions for moving the ultrasound imaging device. As another example, if the statistical model has not been trained on sequences of ultrasound images collected by ultrasound imaging devices moving beyond the threshold velocity, the statistical model may not provide accurate instructions based on ultrasound images collected by an ultrasound imaging device moving beyond the threshold velocity. Providing instructions to a user to slow down movement of the ultrasound imaging device may help to increase the accuracy of instructions provided by the statistical model. As another example, moving an ultrasound imaging device too fast may result in blurry ultrasound images, and providing instructions to a user to slow down movement of the ultrasound imaging device may help to improve the quality of ultrasound images collected.

To provide the instruction for slowing the velocity of the ultrasound imaging device, the processing device may display the instruction on a display screen (e.g., display screen 108) of the processing device. For example, if the processing device is a smartphone coupled to the ultrasound imaging device by a cable, the smartphone may display the instruction on its display screen. The displayed instruction may include words (e.g., "Slow down"). In some embodiments, the processing device may generate audio containing the instructions from speakers (e.g., speakers included in the processing device). The instruction provided in act 508 may be provided in conjunction with the instructions provided in acts 212A-C and 216A. For example, when a user moves the ultrasound imaging device in response to the instructions provided in acts 212A-C or 216A, if the user moves the ultrasound imaging device too fast, the instruction of act 508 may be provided to slow down movement of the ultrasound imaging device.

In some embodiments, the processing device may determine whether ultrasound data and motion and/or orientation data indicates a velocity of the ultrasound imaging device that is less than a threshold velocity, and if so, provide an instruction to speed up movement of the ultrasound imaging device. This may be helpful if the statistical model has not been trained on sequences of ultrasound images collected by ultrasound imaging devices moving below the threshold velocity, as the statistical model may not provide accurate instructions based on ultrasound images collected by an ultrasound imaging device moving below the threshold velocity. Providing instructions to a user to speed up movement of the ultrasound imaging device may help to increase the accuracy of instructions provided by the statistical model.

The above description has described the processes 200A-C and 500 as being performed by a processing device in operative communication with an ultrasound imaging device. However, it should be appreciated that any steps of the processes 200A-C and 500 may also be performed by the ultrasound imaging device itself or any combination of devices in operative communication with the ultrasound imaging device and each other. For example, when the process is performed by the ultrasound imaging device 114 itself, the ultrasound imaging device 114 may include the processor 110, the memory 112, the display screen 108, the input device 118, and/or the camera 106. The processor 110 of the ultrasound imaging device 114 may execute one or more processor-executable instructions stored in one or more non-transitory computer-readable storage media (e.g., the memory 112 of the ultrasound imaging device), which may serve as non-transitory computer-readable storage media storing processor-executable instructions for execution by the processor 110. Additionally, the embodiments described herein may also be applied to ultrasound devices used for other purposes besides imaging, such as ultrasound devices for treatment (e.g., high-intensity focused ultrasound (HIFU)).

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Aspects of the technology described herein relate to the application of automated image processing techniques to analyze images, such as ultrasound images. In some embodiments, the automated image processing techniques may include machine learning techniques such as deep learning techniques. Machine learning techniques may include techniques that seek to identify patterns in a set of data points and use the identified patterns to make predictions for new data points. These machine learning techniques may involve training (and/or building) a model using a training data set to make such predictions.

Deep learning techniques may include those machine learning techniques that employ neural networks to make predictions. Neural networks typically include a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input, for example, to weight some inputs higher than others. Example transfer functions that may be employed include step functions, piecewise linear functions, and sigmoid functions. These neurons may be organized into a plurality of sequential layers that each include one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may include a set of example inputs and an answer associated with each input. For example, the training data may include a plurality of ultrasound images or sets of raw acoustical data that are each labeled with an instruction for moving an ultrasound imaging device from the position/orientation where the inputted ultrasound data was collected to a target position/orientation. In this example, the ultrasound images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

Once the training data has been created, the training data may be loaded to a database (e.g., an image database) and used to train a neural network using deep learning techniques. Once the neural network has been trained, the trained neural network may be deployed to one or more processing devices.

Figure 8:
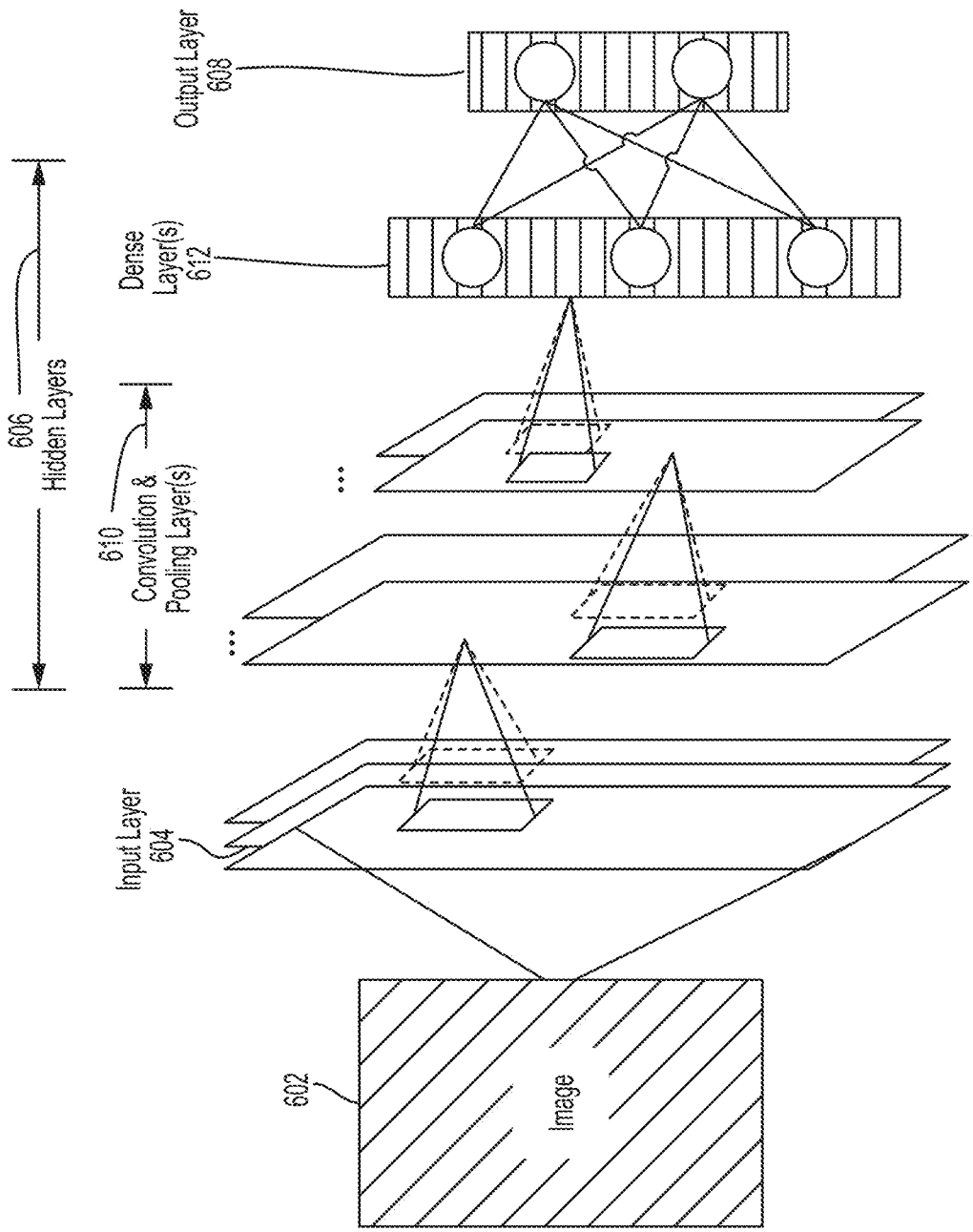
FIG. 8 illustrates an example convolutional neural network that is configured to analyze an image.

In some applications, a neural network may be implemented using one or more convolution layers to form a convolutional neural network. An example convolutional neural network is shown in FIG. 8 that is configured to analyze an image 602. As shown, the convolutional neural network includes an input layer 604 to receive the image 602, an output layer 608 to provide the output, and a plurality of hidden layers 606 connected between the input layer 604 and the output layer 608. The plurality of hidden layers 606 includes convolution and pooling layers 610 and dense layers 612.

The input layer 604 may receive the input to the convolutional neural network. As shown in FIG. 8, the input the convolutional neural network may be the image 602. The image 602 may be, for example, an ultrasound image.

The input layer 604 may be followed by one or more convolution and pooling layers 610. A convolutional layer may include a set of filters that are spatially smaller (e.g., have a smaller width and/or height) than the input to the convolutional layer (e.g., the image 602). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 610 may be followed by dense layers 612. The dense layers 612 may include one or more layers each with one or more neurons that receives an input from a previous layer (e.g., a convolutional or pooling layer) and provides an output to a subsequent layer (e.g., the output layer 608). The dense layers 612 may be described as "dense" because each of the neurons in a given layer may receive an input from each neuron in a previous layer and provide an output to each neuron in a subsequent layer. The dense layers 612 may be followed by an output layer 608 that provides the outputs of the convolutional neural network. The outputs may be, for example, instructions to translate, rotate, and tilt an ultrasound imaging device. The output layer 608 may provide the outputs to translate, rotate, and tilt the ultrasound imaging device simultaneously and independently of each other. A processing device receiving the outputs from the output layer 608 may only choose to provide to a user one of these outputs at a time. For example, once the ultrasound imaging device is in a default orientation, the processing device may first provide translation instruction outputs from the neural network, then provide rotation instruction outputs from the neural network once there are no further translation instructions, and then provide tilt instruction outputs from the neural network once there are no further rotation instructions.

It should be appreciated that the convolutional neural network shown in FIG. 8 is only one example implementation and that other implementations may be employed. For example, one or more layers may be added to or removed from the convolutional neural network shown in FIG. 8. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

For further description of deep learning techniques, see U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application), which is incorporated by reference herein in its entirety. In any of the embodiments described herein, instead of or in addition to using one or more convolutional neural networks, fully connected neural networks, random forests, support vector machines, linear classifiers, and/or other machine learning models may be used.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
   a processing device in operative communication with an ultrasound imaging device, the processing device configured to provide instructions for adjusting an orientation and position of the ultrasound imaging device from an initial orientation and an initial position to a target orientation different than the initial orientation and a target position different than the initial position, as part of which the processing device is configured to:
   provide, when the ultrasound imaging device is in the initial position different than the target position, a first instruction for rotating or tilting the ultrasound imaging device from the initial orientation to a default orientation different than both the initial orientation and the target orientation while maintaining the ultrasound imaging device at the initial position, where the first instruction does not include instructions for translating movement;
   after providing the first instruction, and based on determining that the ultrasound imaging device is in the default orientation, provide a second instruction for translating the ultrasound imaging device from the initial position to the target position while maintaining the ultrasound imaging device in the default orientation, wherein the second instruction does not include instructions for rotating or tilting movement; and
   after providing the second instruction, and based on determining that the ultrasound imaging device is in the target position, provide a third instruction for rotating or tilting the ultrasound imaging device from the default orientation to the target orientation while maintaining the ultrasound imaging device at the target position, wherein the third instruction does not include instructions for translating movement, and
   wherein the processing device provides the first, second, and third instructions arranged in a sequenced order.

2. The apparatus of claim 1, wherein the processing device is configured, when providing the first instruction for rotating or tilting the ultrasound imaging device from the initial orientation to the default orientation, to:
   receive motion and/or orientation data from the ultrasound imaging device, wherein the motion and/or orientation data provides an indication of a motion and/or orientation of the ultrasound imaging device;
   determine, based on the motion and/or orientation data, that the ultrasound imaging device is not in the default orientation; and
   provide the first instruction for rotating or tilting the ultrasound imaging device to the default orientation based on the motion and/or orientation data.

3. The apparatus of claim 2, wherein the ultrasound imaging device is configured to generate the motion and/or orientation data using one or more of an accelerometer, a gyroscope, or a magnetometer on the ultrasound imaging device.

4. The apparatus of claim 1, wherein the default orientation comprises:
   a longitudinal axis of the ultrasound imaging device being parallel to gravity; and
   a longitudinal axis of a sensor of the ultrasound imaging device being perpendicular to a longitudinal axis of a subject being imaged.

5. The apparatus of claim 1, where the processing device is further configured to:
   receive motion and/or orientation data from the ultrasound imaging device, wherein the motion and/or orientation data provides an indication of a motion and/or orientation of the ultrasound imaging device; and determine, based on the motion and/or orientation data, that the ultrasound imaging device is in the default orientation.

6. The apparatus of claim 1, wherein the processing device is configured, when providing the second instruction for translating the ultrasound imaging device to the target position, to:
receive first ultrasound data from the ultrasound imaging device;
determine, based on the first ultrasound data, that the ultrasound imaging device is not at the target position; and
provide the second instruction for translating the ultrasound imaging device to the target position based on the first ultrasound data.

7. The apparatus of claim 6, wherein the processing device is configured, when providing the second instruction for translating the ultrasound imaging device to the target position based on the first ultrasound data, to:
input the first ultrasound data to a statistical model configured to output instructions for moving the ultrasound imaging device based on inputted ultrasound data.

8. The apparatus of claim 7, wherein the processing device is further configured to:
receive, from the statistical model, an instruction corresponding to translating the ultrasound imaging device and an instruction corresponding to rotating or tilting the ultrasound imaging device; and
provide, as the second instruction, the instruction corresponding to translating the ultrasound imaging device and not the instruction corresponding to rotating or tilting the ultrasound imaging device.

9. The apparatus of claim 7, wherein the statistical model has been trained on training ultrasound data which was collected by one or more other ultrasound imaging devices in the default orientation and/or the target position.

10. The apparatus of claim 1, wherein the processing device is further configured to:
receive, subsequent to providing the second instruction, motion and/or orientation data from the ultrasound imaging device, wherein the motion and/or orientation data provides an indication of a motion and/or orientation of the ultrasound imaging device;
determine, based on the motion and/or orientation data, that the ultrasound imaging device is not in the default orientation; and
provide a fourth instruction for moving the ultrasound imaging device to the default orientation based on the motion and/or orientation data.

11. The apparatus of claim 1, wherein the processing device is further configured to:
after providing the second instruction for translating the ultrasound imaging device to the target position, receive first ultrasound data from the ultrasound imaging device; and
determine, based on the first ultrasound data, that the ultrasound imaging device is at the target position.

12. The apparatus of claim 11, wherein the processing device is configured, when providing the third instruction for rotating or tilting the ultrasound imaging device to the target orientation, to:
receive second ultrasound data from the ultrasound imaging device;
determine, based on the second ultrasound data, that the ultrasound imaging device is not in the target orientation; and
provide the third instruction for rotating or tilting the ultrasound imaging device to the target orientation based on the second ultrasound data.

13. The apparatus of claim 12, wherein the processing device is configured, when providing the third instruction for rotating or tilting the ultrasound imaging device to the target orientation based on the second ultrasound data, to:
input the second ultrasound data to a statistical model configured to output instructions for moving the ultrasound imaging device based on inputted ultrasound data.

14. The apparatus of claim 13, wherein the processing device is further configured to:
receive, from the statistical model, an instruction corresponding to translating the ultrasound imaging device and an instruction corresponding to rotating or tilting the ultrasound imaging device; and
provide, as the third instruction, the instruction corresponding to rotating or tilting the ultrasound imaging device and not the instruction corresponding to translating the ultrasound imaging device.

15. The apparatus of claim 13, wherein the statistical model has been trained on training ultrasound data which was collected by one or more other ultrasound imaging devices in the default orientation and/or the target position.

16. The apparatus of claim 1, wherein the processing device is further configured to:
receive, subsequent to providing the third instruction, ultrasound data from the ultrasound imaging device;
determine, based on the ultrasound data, that the ultrasound imaging device is not in the target position; and
provide a fourth instruction for moving the ultrasound imaging device to the target position based on the ultrasound data.

17. The apparatus of claim 1, wherein the processing device is further configured to:
receive ultrasound data from the ultrasound imaging device; and
determine, based on the ultrasound data, that the ultrasound imaging device is in the target orientation.

18. A method, comprising:
providing, by a processing device in operative communication with an ultrasound imaging device that is in an initial orientation different than a target orientation and an initial position different than a target position, a first instruction for rotating or tilting the ultrasound imaging device from the initial orientation to a default orientation different than the initial orientation and the target orientation while maintaining the ultrasound imaging device at the initial position, where the first instruction does not include instructions for translating movement;
based on determining that the ultrasound imaging device is in the default orientation, providing a second instruction for translating the ultrasound imaging device from the initial position to the target position while maintaining the ultrasound imaging device in the default orientation, wherein the second instruction does not include instructions for rotating or tilting movement; and
based on determining that the ultrasound imaging device is in the target position, providing a third instruction for rotating or tilting the ultrasound imaging device from the default orientation to the target orientation while maintaining the ultrasound imaging device at the target position, wherein the third instruction does not include instructions for translating movement, and wherein the first, second, and third instructions are arranged in a sequenced order.

19. The method of claim 18, further comprising, when providing the first instruction for rotating or tilting the ultrasound imaging device to the default orientation:
   receiving motion and/or orientation data from the ultrasound imaging device, wherein the motion and/or orientation data provides an indication of a motion and/or orientation of the ultrasound imaging device;
   determining, based on the motion and/or orientation data, that the ultrasound imaging device is not in the default orientation; and
   providing the first instruction for rotating or tilting the ultrasound imaging device to the default orientation based on the motion and/or orientation data.

20. The method of claim 18, further comprising:
   receiving, subsequent to providing the second instruction, motion and/or orientation data from the ultrasound imaging device, wherein the motion and/or orientation data provides an indication of a motion and/or orientation of the ultrasound imaging device;
   determining, based on the motion and/or orientation data, that the ultrasound imaging device is not in the default orientation; and
   providing a fourth instruction for moving the ultrasound imaging device to the default orientation based on the motion and/or orientation data.

* * * * *